(12) United States Patent
Niederjohn et al.

(10) Patent No.: US 6,168,577 B1
(45) Date of Patent: Jan. 2, 2001

(54) DIRECTED STREAM BLOWER FOR CLEARING A SURGICAL SITE

(75) Inventors: James W. Niederjohn, Fremont; Harry L. Green, II, Santa Cruz; Eugene E. Reis, San Jose, all of CA (US)

(73) Assignee: Cardiothoracic Systems, Inc., Cupertino, CA (US)

( * ) Notice: Under 35 U.S.C. 154(b), the term of this patent shall be extended for 0 days.

(21) Appl. No.: 09/237,088

(22) Filed: Jan. 25, 1999

(51) Int. Cl.$^7$ .......................... A61M 37/00; A61M 5/00
(52) U.S. Cl. .................. 604/23; 604/24; 604/250
(58) Field of Search .................. 604/19, 23, 24, 604/27, 30, 34, 250, 248; 128/200.14; 433/80

(56) References Cited

U.S. PATENT DOCUMENTS

| | | |
|---|---|---|
| 4,108,178 | 8/1978 | Betush . |
| 4,673,161 | 6/1987 | Flynn et al. . |
| 4,869,457 | * 9/1989 | Ewerlof ..................... 251/6 |
| 4,892,526 | 1/1990 | Reese . |
| 4,941,872 | 7/1990 | Felix et al. . |
| 5,203,769 | 4/1993 | Clement et al. . |
| 5,242,386 | 9/1993 | Holzer . |
| 5,336,170 | 8/1994 | Salerno et al. . |
| 5,489,280 | 2/1996 | Russell . |
| 5,820,373 | * 10/1998 | Okano et al. ..................... 433/80 |
| 5,830,214 | 11/1998 | Flom et al. . |
| 5,846,219 | 12/1998 | Vancaillie . |

OTHER PUBLICATIONS

Simon P. Hoerstrup, Mario L. Lachat, Gregor Zund, Paul R. Vogt, and Marko I. Turina. "Improved Visualization in Minimally Invasive Coronary Bypass Grafting," Ann. Thorac Surg 1998; 66:963–4, 1998.

Michael Maddaus, Imtiaz Ali, Peter L. Birnbaum, Anthony L. Panos, and Tomas A. Salerno. "Coronary Artery Surgery Without Cardiopulmonary Bypass: Usefulness of the Surgical Blower–Humidifier." Journal of Cardiac Surgery, vol. 7:348–350 1992.

William R. Burfiend, Jr., Francis G. Duhaylongsod, Brian H. Annex and David Samuelson. "High–Flow Gas Insufflation to Facilitate MIDCABG: Effects on Coronary Endothelium." Ann Thorac Surg: 66:1246–1249, 1998.

* cited by examiner

Primary Examiner—Mark Bockelman
Assistant Examiner—Michael J Hayes

(57) ABSTRACT

A directed stream blower is provided for removing materials from a surgical site, thus improving the visibility of the surgical site. Preferably, the directed stream blower provides a directed stream of pressurized gas combined and intermixed with a sterile fluid which may be used to clear or wash away blood, debris, particulate, or other materials from the target surgical site. The directed stream blower may be provided with flow control positioned directly on the handle for convenient one-handed operation during use.

19 Claims, 6 Drawing Sheets

DIRECTED STREAM BLOWER FOR CLEARING A SURGICAL SITE

FIELD OF THE INVENTION

The present invention relates generally to surgical instruments, and more particularly to a surgical apparatus for providing a directed stream of gas and/or fluid to a surgical site to improve visibility.

BACKGROUND OF THE INVENTION

A difficult aspect of many surgical procedures is obtaining and maintaining clear and unobstructed visibility at the surgical site. Accordingly, the instruments and fixtures used in a surgical setting are meticulously designed and selected to ensure that the surgeons have optimum visual access to the surgical site. In most instances, irrigation and suction are used in one form or another to wash away and remove unwanted or undesirable material, fluids, or other particulate. In prolonged surgical procedures, irrigation is also useful in preventing the deleterious effects of tissue desiccation.

Visibility requirements are particularly acute when the surgery involves particularly delicate or small structures, such as those routinely encountered in vascular or neurological surgery. In a vascular anastomosis procedure, for example, even small amounts of fluid or other material can significantly effect the surgeons view of the anastomotic site. Blood flow from the surrounding tissues or from the vessels themselves is particularly problematic for visualization of the surgical site during an anastomosis. In such procedures, standard liquid irrigation alone is often ineffective for clearing the surgical site.

Devices using a directed gas or fluid stream to obtain a clear view of the surgical site are known. For example, U.S. Pat. No. 5,336,170 to Salerno et al. discloses a surgical site visualization wand which has a fluid delivery conduit having a fan shaped tip for delivering a pressurized gas to a target site. The visualization wand may also have a humidification or moisturizing conduit for the selective introduction of a sterile liquid in the form of a mist carried by and intermixed with the gas stream to the target site. Such arrangements tend to have the improved ability to blow away fluid or debris without desiccating tissue.

One problem with the directed stream visualization devices known in the art, however, is that they are cumbersome to operate, offering inadequate gas and liquid flow control. If the flow rate of the gas supply is too low, it will not adequately clear the targeted site of undesired material. If the gas stream is delivered at an excessive flow rate or pressure it tends to cause a certain amount of spattering of the cleared material and may displace or damage the delicate tissue structures under operation. If the flow rate of the liquid is too high it may over-irrigate the site; too low and the surrounding tissue may become desiccated.

Typically, such visualization devices offer flow control only in the form of separate mechanical clamps at the liquid supply line and at the gas supply line. To adjust the flow rate of either the gas or the liquid, the user is required to distract their attention from the surgical site, locate the appropriate clamp along the supply tubing, manipulate the clamp to effectuate a change in flow rate, observe whether the adjustment has had the desired effect on the characteristics of the flow emanating from the device, and then return the device, and their attention, to the surgical site.

In fact, the process of closing or adjusting the flow rates of such devices is, in many cases, so cumbersome that it has become common to simply leave the device on and flowing for the duration of the procedure. This results in an unacceptable waste of both pressurized gas and sterile liquid. Moreover, the continuous flow of gas and liquid throughout the duration of the surgical procedure may cause the supply of gas or liquid to run out to the detriment of the surgeon, and ultimately the patient. While members of the surgical team are distracted with the task of locating and connecting a new supply, the surgeon must endure diminished visibility at the surgical site.

In view of the foregoing, it would be desirable to have a directed stream blower device for improving surgical site visualization having a convenient flow control for single-handed, undistracted operation. Most desirably, the flow control would not only allow in-use flow rate adjustment, but would also allow the fluid and gas flow to be substantially stopped and started as desired during a surgical procedure. It would be further desirable to have these features in a directed stream blower which is of simple construction and preferably disposable.

SUMMARY OF THE INVENTION

The present invention involves a directed stream surgical blower for removing unwanted fluid and other materials from a surgical site. Preferably, the blower provides an intermixed stream of gas and fluid which may be directed to the surgical site to remove blood, debris, particulate, or other undesirable material from a target surgical site.

In one aspect of the present invention, the directed stream blower is provided with a distally located flow control mechanism configured for convenient one-handed operation of the flow control while the blower is being used to actively clear a surgical site. This allows the stream directed at a target surgical site to be adjusted or interrupted by the user during use without distraction. Preferably, the directed stream blower or the flow control mechanism or both have a construction suitable for disposable use.

In one embodiment, the invention involves a directed stream blower having an elongated flexible tube having a first lumen and a separate and independent second lumen and a handle. The handle has an interior passage for receiving a length of the flexible tube, a surface adapted to support at least a portion of the length of the tube, and a roller which is positionable in relation to the surface. A portion of the length of the flexible tube is positioned within the handle passage between the surface and the roller such that movement of the roller closer to the surface at least partially clamps the flexible tube. Such clamping effectively reduces the cross-sectional flow area or either the first lumen or the second lumen, or both. In one embodiment, the first lumen and the second lumen are coaxial.

In a preferred embodiment, the flexible tube includes an outer tube and an inner tube. The outer tube has an inside diameter and a central lumen therein and the inner tube has an outside diameter. The inner tube is positioned within the central lumen of the outer tube. In this configuration, the second lumen of the flexible tubing is simply the lumen within the inner tube and the first lumen of the flexible tubing is the space between the inside diameter of the outer tube and the outside diameter of the inner tube. The outer tube and the inner tube may be made from different materials having different properties.

In one aspect of the present invention, the roller is substantially cylindrical having a central axis and a central hub shaft generally concentric with the central axis. The handle may comprise at least one slot oriented at an angle to the surface. The hub shaft of the roller may be constrained within the slot or slots. In a preferred embodiment, the hub shaft has a first end and a second end and the handle has a first slot and a second slot parallel to the first slot. The first end of the hub shaft may be constrained within the first slot and the second end within the second slot. The slots provide support for the roller on both sides as well as constraining the roller to movement in accordance with the shape or path of the slot.

In one embodiment, the angle between the surface supporting the flexible tube and the slot in which the roller rides is preferably in the range from about 4° to about 20°, more preferably between about 4° to about 8°. At one end of the slot the roller will be at a first distance from the surface and at the other end the roller is spaced at a second distance from the surface.

Preferably, the proximal end of the first lumen is connected to a source of pressurized gas and the proximal end of the second lumen is connected to a source of fluid. In a preferred embodiment, the surgical blower further comprises a malleable tube having a proximal portion positioned with the interior passage of the handle and distal end for placement adjacent the surgical site to be cleared. Preferably, the distal end of the first lumen is fluidly coupled to the proximal portion of the malleable tube. The second lumen preferably extends through at least a portion of the malleable tube, preferably terminating distal of said malleable tube. In one embodiment, an atraumatic tip may be secured to the distal end of the malleable tube.

The present invention also involves a surgical blower for providing a directed stream for clearing a surgical site comprising a handle having a surface or ramp adapted to support a length of flexible tubing and an articulating actuator associated with the handle. The actuator is moveable relative to the surface from at least a first position at a first distance from the surface to a second position at a second distance relative to the surface. A section of flexible tubing is positioned between the surface and the actuator, the flexible tubing having an outside diameter greater than the second distance. Thus, the flexible tube is pinched or clamped to a greater extent as the actuator is moved closer to the surface.

In one embodiment, the articulating actuator is a roller constrained within at least one slot, the slot being at an angle relative to the surface. The roller is preferably cylindrical in shape having an outer surface. The roller preferably has a plurality of teeth formed in the outer surface.

In a preferred embodiment, the first lumen is in fluid communication with a source of pressurized gas and the second lumen is in fluid communication with a source of sterile fluid. Preferably, the first and second lumen are coaxial.

The present invention further involves a surgical blower for providing a directed stream for clearing a surgical site which includes a handle, a malleable tube, and a multilumen flexible tube. The handle preferably has a proximal opening, a distal opening and a channel extending therebetween. The malleable tube has a proximal end portion secured within said channel and a distal end portion for placement adjacent to the surgical site. The elongated flexible tube has a first lumen and a second lumen, preferably in a coaxial relationship. The proximal end of the first lumen being connected to a source of pressurized gas and the proximal end of the second lumen being connected to a source of fluid. The distal end of the first lumen is fluidly coupled to the malleable tube. The second lumen extends through at least a portion of the malleable tube, preferably terminating distal of the malleable tube. The malleable tube is preferably made of stainless steel and may have a polymeric layer covering substantially all of the malleable tube.

In a preferred embodiment, the handle further includes a ramp, at least one slot at an angle with respect to the ramp, and a roller having a central hub constrained within the slot for movement from at least a first position at a first distance from the ramp to a second position at a second distance from the ramp. The flexible tube, positioned between the ramp and the roller, has an outside dimension or diameter greater than the second distance.

These and other features and advantages of the present invention will be apparent from the following detailed description, accompanying figures, and appended claims.

DETAILED DESCRIPTION

Figure 1A:
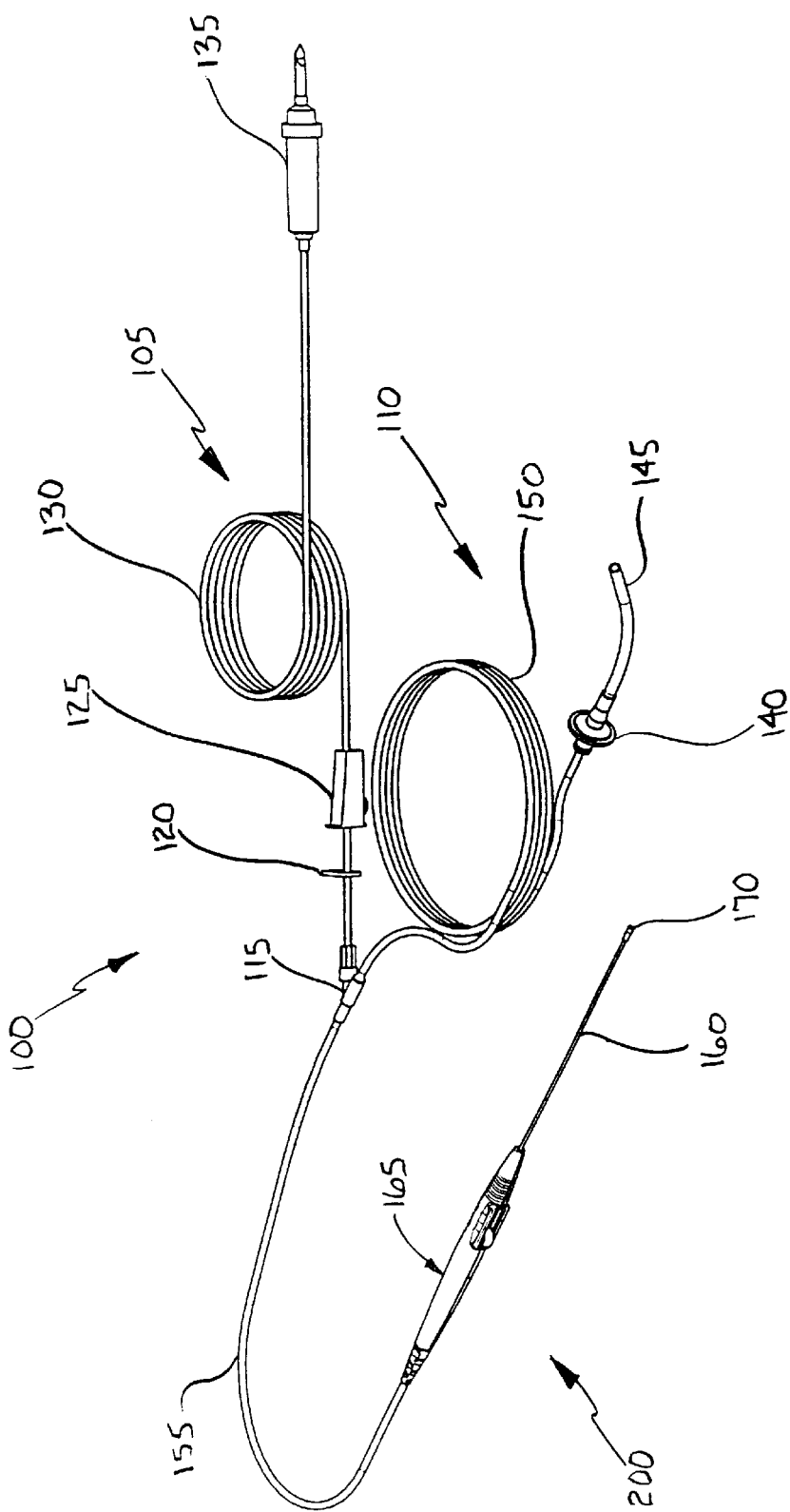
FIG. 1A is a perspective view of a directed stream blower system constructed according to the principles of the present invention.

Referring to the drawings in detail wherein like numerals indicate like elements, the present invention generally involves a directed stream blower for removing unwanted materials from a surgical site, thus improving the visibility at the surgical site. Preferably, the directed stream blower provides a directed stream of pressurized gas combined with a sterile liquid or fluid which may be used to clear or wash away blood, debris, particulate, or other material from a desired surgical site.

An important aspect of the present invention involves a directed stream blower having a distally located flow control mechanism. In a preferred embodiment, the flow control is provided on a distal handle or handpiece configured for convenient, single-handed operation. Thus, the flow of the directed stream emanating from the blower may be adjusted while the handpiece is comfortably grasped in one hand and being manipulated to clear a surgical site. This allows the stream directed at a target surgical site to be adjusted or interrupted by the user while the site is being actively cleared by the blower.

The flow control may involve separate distal controls for the gas and the fluid. More preferably, the flow control involves a single flow control interface or actuator which may provide proportional flow adjustment of both gas and fluid, differential adjustment of the gas flow relative to the fluid flow, the capability to substantially stop or interrupt the flow of both the gas and the fluid, or any desirable combination thereof.

Another important aspect of the present invention involves a directed stream blower having a reliable, elegant, low cost construction, desirably suitable for disposable use. Blower instruments having increased cost and complexity are generally not acceptable as disposable instruments. Thus, the directed stream blower of the present invention preferably achieves the desired flow control without resort to complicated and expensive manifolds, valves, or mechanisms.

FIG. 1A illustrates a directed stream blower system constructed according to the principles of the present invention. Blower system 100 preferably includes fluid supply assembly 105, gas supply assembly 110, and distal delivery unit 200. Distal delivery unit 200 is connected to fluid supply assembly 105 and gas supply assembly 110 through Y-connector 115 and multi-lumen tubing 155. Distal delivery unit 200 preferably has a handpiece assembly 165 and a distal delivery shaft 160 extending therefrom and having distal tip 170 through which the gas and fluid are directed towards a target surgical site. Preferably, delivery shaft 160 is shapeable or malleable so that the angle of at least a portion of delivery shaft 160 and distal tip 170 relative to the handpiece assembly can be easily manipulated to improve access and maneuverability.

The fluid supply assembly may be any type or combination of tubing and connectors which may be required to connect the directed stream blower to an appropriate source of liquid or fluid. In a preferred embodiment, fluid supply assembly 105 is configured for connection to a conventional bag of sterile saline (not shown). Fluid supply assembly 105 has a length of flexible fluid tubing 130 fluidly coupled distally to Y-connector 115 and proximally to a conventional IV spike and chamber 135. Fluid tubing 130 may optionally be provided with pinch clamp 120 to allow complete flow stoppage and roller clamp 125 to adjust the flow rate of the sterile saline supply. A conventional pressure cuff (not shown) may be used in connection with the bag of sterile saline to regulate the delivery pressure of the sterile saline.

The gas supply assembly may be any type or combination of tubing and connectors which may be required to connect the directed stream blower to an appropriate regulated source of pressurized gas, such as compressed medical air, carbon dioxide, nitrogen, or other suitable gas. In a preferred embodiment, gas supply assembly 110 includes a length of flexible gas tubing 150, a filter 140, and a section of braided tubing 145 to ensure a secure connection to the gas supply. Preferably, filter 140 is an antibacterial filter in the range of about 0.1 $\mu$m to about 0.2 $\mu$m.

The flexible fluid tubing 130 and flexible gas tubing 150 are connected to two of the branches of Y-connector 115. Multi-lumen tubing 155 is connected to the third branch of Y-connector 115. Y-connector 115 fluidly connects flexible fluid tubing 130 to a first independent lumen within multi-lumen tubing 155 and fluidly connects flexible gas tubing 150 to a separate and independent second lumen within multi-lumen tubing 155. To keep the surgical area from becoming cluttered with multiple hoses, Y-connector 115 is preferably positioned a sufficient distance away from distal delivery unit 200, typically in the range of about 15 inches (38.1 cm) to about 50 inches (127 cm) or more. In a preferred embodiment, the distance from the proximal end of distal delivery unit 200 to Y-connector 115 at least 20 inches (50.8 cm), more preferably at least 30 inches (76.2 cm).

Figures 2A, 2B, 2C, 2D:
FIGS. 2A, 2B, 2C and 2D are cross-sectional views of multi-lumen flexible tubing showing exemplar gas and fluid lumen arrangements.

Multi-lumen tubing 155 generally has at least two independent and separate lumen for separately channeling the pressurized gas and the fluid. The lumen may be configured in a number of ways, examples of which are shown in FIGS. 2A–2D. In the embodiment shown in FIG. 2A, multi-lumen tubing 155 is a coaxial arrangement of outer tube 205 and inner tube 210 which form an outer gas flow lumen 215 and inner fluid flow lumen 220. FIG. 2B shows an alternate coaxial construction in which inner tube 211 having inner fluid flow lumen 221 is held in place within outer tube 206 by way of longitudinal ribs 223 which may separate outer gas flow lumen 216 into more than one conduit as shown. In the embodiment shown in FIG. 2C, multi-lumen tubing 155 has an outer wall 225 and septum 227 forming independent gas flow lumen 230 and liquid flow lumen 235. In the embodiment shown in FIG. 2D, multi-lumen tubing 155 has wall material 240 forming a liquid flow lumen 245 having a generally circular cross-section and a separate gas flow lumen 250.

In a preferred embodiment, multi-lumen tubing 155 is configured having outer tube 205 and inner tube 210 in a coaxial relationship as shown in FIG. 2A. This arrangement tends to simplify the necessary tubing connections and advantageously allows the use of different materials for outer tube 205 and inner tube 210 without complication. Thus, outer tube 205 and inner tube 210 may each be made of a material having properties (i.e., flexural modulus, burst strength, gas permeability, water absorption, kink-resistance, cost, etc.) selected to ensure their individual optimum performance.

When outer 205 and inner tube 210 are configured to deliver pressurized gas and sterile saline, respectively, outer tube 205 is preferably made from polyurethane and inner tube 210 is made from nylon. Typically, the cross-sectional area of the gas flow lumen is considerably greater than the cross-sectional area of the fluid flow lumen, generally by a factor of two or more. In a preferred embodiment, the cross-sectional area of gas flow lumen 215 is in the range of about 0.003 inches$^2$ (0.076 mm$^2$) to about 0.01 inches$^2$ (0.254 mm$^2$). The cross-sectional flow area of fluid flow lumen 220 is preferably in the range of about 0.0003 inches$^2$ (0.00762 mm$^2$) to about 0.001 inches$^2$ (0.0254 mm$^2$) or more. In one embodiment, outer tube 205 is preferably made from a polyurethane having a durometer in the range of about 70 Shore A to about 90 Shore A, an outside diameter of about 0.159 inches (4.04 mm), and a wall thickness of about 0.032 inches (0.813 mm). Inner tube 210 is preferably made from Nylon 12 having an inside diameter of about 0.027 inches (0.686 mm) and a wall thickness of about 0.005 inches (0.127 mm).

Figure 1B:
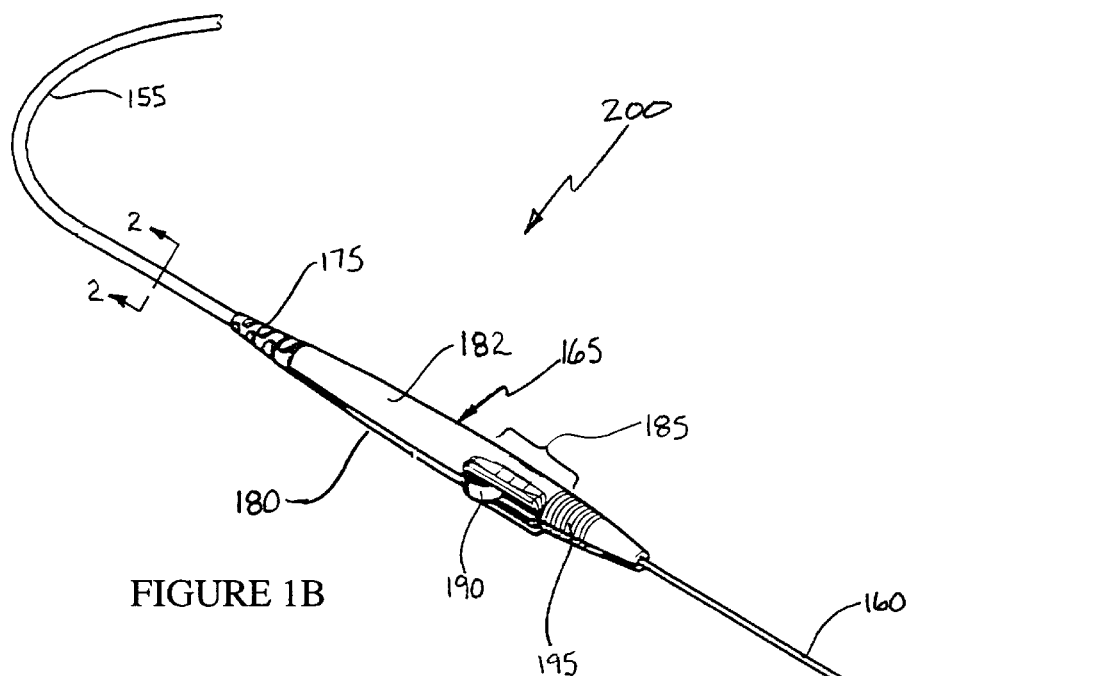
FIG. 1B is a perspective view illustrating the distal delivery unit of the directed stream blower system of FIG. 1A.

A magnified view of distal delivery unit 200 is shown in FIG. 1B. The handle area is generally shaped and configured to be comfortably held in one hand. Preferably, handpiece assembly 165 has an elongated shape that can be easily grasped by the user for precise positioning and control of the distal tip 170 at or near the surgical site. In a preferred embodiment, handpiece assembly 165 houses a flow control mechanism which includes an easily accessible, articulating actuator that may be operated simultaneously by the same hand grasping handpiece assembly 165.

Multi-lumen tubing 155 extends to handpiece assembly 165. The handpiece assembly may be constructed as a sealed manifold, having gas and fluid lumen, to which multi-lumen tubing 155 could be directly connected. Preferably, however, handpiece assembly 165 is constructed to have a central cavity or passageway allowing a length of multi-lumen tubing 155 to pass partially or completely therethrough. To help reduce kinking of the multi-lumen tubing 155 in the area where it enters handpiece assembly 165, a flexible strain relief 175 may optionally be included.

In one embodiment, multi-lumen tubing 155 passes through substantially the entire length of handpiece assembly 165, exiting the distal end of handpiece assembly 165, and having a distal length sufficient to access the surgical site. In that case, distal delivery shaft 160 is simply a distal section of multi-lumen tubing 155. The distal section of multi-lumen tubing 155 serving as delivery shaft 160 may be made stiffer and/or shapeable by reinforcing or embedding it with, for example, a malleable wire or stylet.

Figure 4:
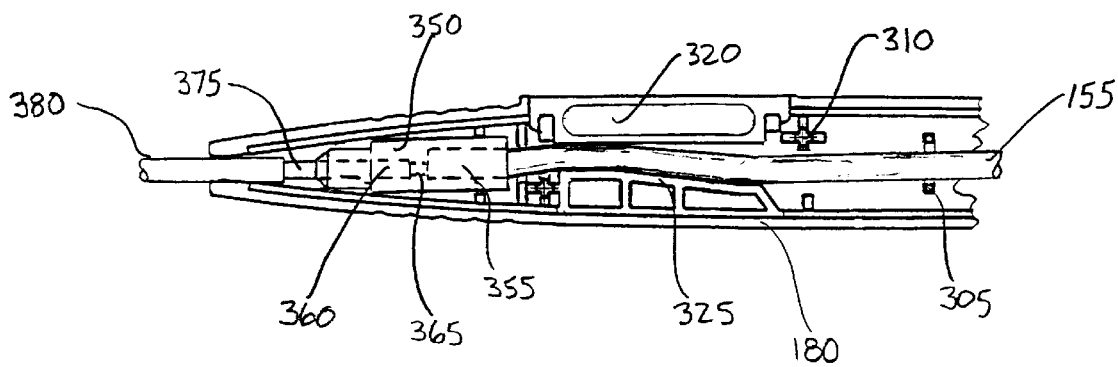
FIG. 4 is a partial plan view illustrating the fluid and gas tubing positioned within the handpiece.

In a preferred embodiment, delivery shaft 160 includes a stiff and preferably malleable tube or shaft 375. Multi-lumen tubing 155 is routed through a portion of handpiece assembly where it is connected to shaft 375 by way of connector 350, as shown in FIG. 4. Connector 350 preferably has a first bore 355 for receiving and sealing or bonding to the outside of multi-lumen tubing 155, a second bore 360 for receiving and sealing or bonding to the outside of shaft 375, and through lumen 365 which allows the fluid lumen (i.e., inner tube 210) from multi-lumen tubing 155 to pass through with sufficient clearance to accommodate the required gas flow.

Shaft 375 is generally constructed of a low-profile tubular material with sufficient stiffness to allow delivery shaft 160 to be effectively maneuvered to clear a surgical site. Preferably, shaft 375 is constructed of a malleable material which allows it to be bent, deformed, or otherwise shaped to optimize access to the target surgical site. In a preferred embodiment, shaft 375 is made from a surgical grade stainless steel tube, preferably AISI 304 stainless steel. The inside diameter of shaft 375 is preferably sized similar to that of through lumen 365.

In a preferred embodiment, shaft 375 may be made from AISI 304 stainless steel having an outside diameter in the range of about 0.05 inches (1.27 mm) to about 0.125 inches (3.18 mm) and a wall thickness in the range of about 0.005 inches (0.127 mm) to about 0.010 inches (0.254 mm). Most preferably, shaft 375 is made from AISI 304 stainless steel having an outside diameter in the range of about 0.070 inches (1.778 mm) to about 0.075 inches (1.905 mm) and a wall thickness of about 0.0075 inches (0.1905 mm).

In a preferred embodiment, handpiece assembly 165 is constructed of two complimentary pieces or halves, for example, first half 180 and second half 182, which may assembled and fixed together in the final configuration shown in FIGS. 1A and 1B. In their assembled state, first and second halves 180 and 182 allow multi-lumen tubing 155 to be securely routed through handpiece assembly 165 and may provide mounting features for securing connector 250 and various other components of distal delivery unit 200.

Figure 3:
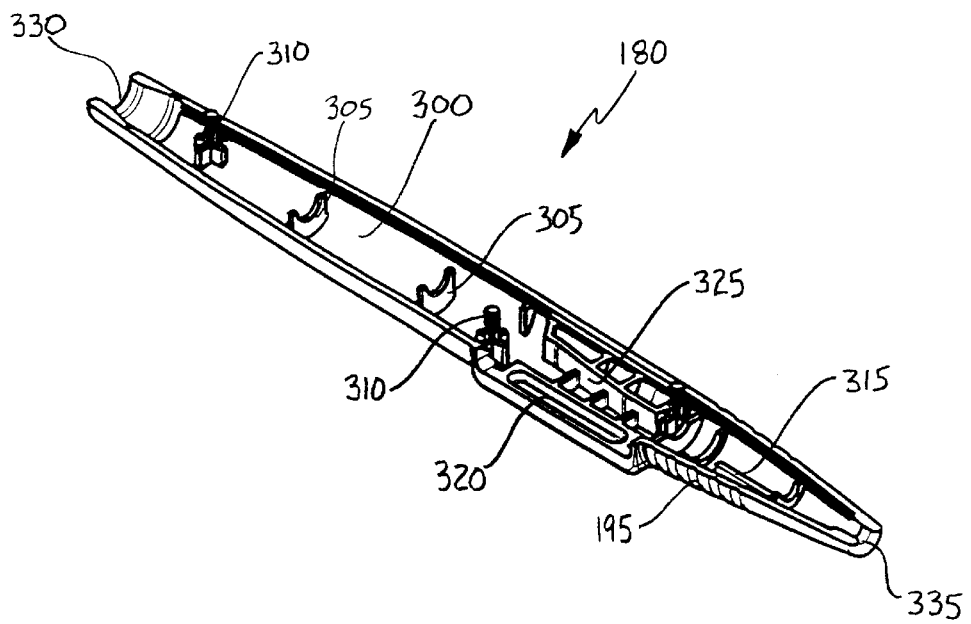
FIG. 3 is a perspective view showing a portion of the handpiece according to one embodiment of the present invention.

Referring to a preferred construction shown in FIGS. 3 and 4, first half 180 is shown having a proximal opening 330 a distal opening 335 and a central hollow or open region 300 extending therebetween. Proximal opening 330 and distal opening 335 preferably form substantially circular openings when mated with complimentary second half 182 to secure flexible strain relief 175 and delivery shaft 160, respectively. Tube retaining ribs 305 and connector retaining rib 315 may be provided within central open region 300 to secure multi-lumen tubing 155 and connector 350 in place within assembled handpiece assembly 165. First and second halves 180 and 182 may be made from any suitable material, preferably an injected molded plastic, most preferably, acrylonitrile-butadiene-styrene (ABS).

To align and secure first and second halves 180 and 182 together, first half 180 may be provided with raised features or posts 310 to be secured within mating recesses or holes (not shown) in second half 182. Posts 310 may be secured in any suitable manner including the use of an interference fit, bonding, adhesive, thermal welding, or the like. Since the pressurized gas and fluid paths are completely contained within multi-lumen tubing 155, connector 350, and shaft 375, there is no need to create a fluid or gas tight seal around any part of first and second halves 180 and 182, or any other part of handpiece assembly 165.

Figure 5:
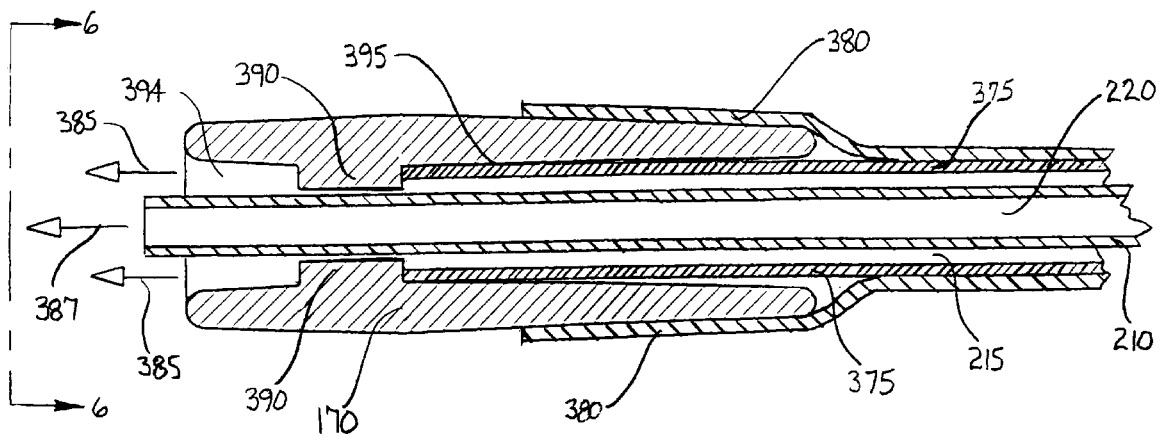
FIG. 5 is a cross-sectional view of the tip region of a directed stream blower device constructed according to the principles of the present invention.
Figure 6:
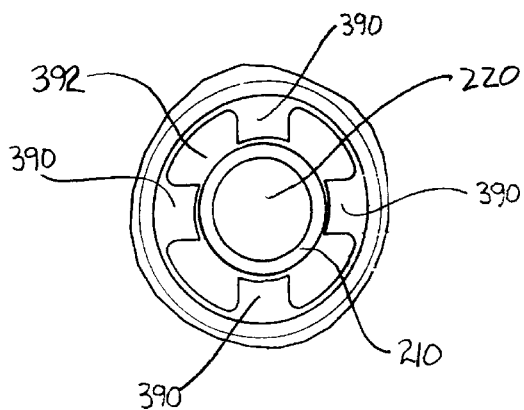
FIG. 6 is a partial plan view in the direction indicated by line 6—6 of FIG. 5 showing the instrument tip.

FIGS. 5 and 6 show a preferred configuration of tip 170. Tip 170 provides an atraumatic covering for the distal end of shaft 375 and may have features to ensure inner tube 210 is properly positioned within gas lumen 215. Tip 170 is preferably made from a relatively soft engineering plastic such as, for example, a polyurethane elastomer.

Tip 170 may generally have a cylindrical shape having a proximal bore 395 for receiving and sealing against or bonding to the distal end of shaft 375. Proximal bore 395 is interrupted by ribs 390 extending radially inward from the interior wall of proximal bore 395. Ribs 390 tend to keep inner tube 210 centered within tip 170. In between ribs 390 are flow passages 392 leading into distal bore 394. In a preferred embodiment, pressurized gas is delivered through lumen 215, flow passages 392 and distal bore 394, exiting distally in the general direction indicated by arrows 385. Sterile liquid is delivered through lumen 220 of inner tube 210 in the general direction of arrow 387.

It is preferred that the distal end of inner tube 210 extends beyond the distal end of bore 394 of tip 170. This configuration is believed to provide a particularly desirable and accurate stream of intermixed gas and fluid for clearing a surgical site.

A polymeric layer, coating or covering 380 may be applied over at least a portion, and preferably all, of shaft 375 and, if desired, tip 170. Covering 380 serves a number of purposes. When covering 380 is applied over at least a portion of tip 370, it provides an added measure of safety to ensure that tip 170 does not become separated from shaft 375. Covering 380 may also serve to inhibit or contain leakage which would otherwise occur if shaft 375 is broken or fractured, for example as a result of severe deformation beyond the limits of the material. Preferably, covering 380 is of a material that tends to reduce the glare or reflection from the various lights directed at the surgical site. In a preferred embodiment, covering 380 is a polyolefin shrink tubing, most preferably having a black or other color or finish which reduces reflection of visible light.

Handpiece assembly 165 has a flow control mechanism preferably positioned towards the distal end of handpiece assembly 165 and having a control or actuator configured for finger or thumb articulation. The flow control mechanism may be any appropriate valve or clamping mechanism capable of restricting or interrupting the flow of the pressurized gas, the fluid, or both. The flow control may involve breaking multi-lumen tubing 155 and inserting a valve in-line. In that case the valve may be any conventional type including, but not limited to, ball, gate, needle, slide, diaphragm, or other suitable valve. Alternatively, the flow control mechanism may operate directly on multi-lumen tubing itself without requiring multi-lumen tubing 155 to be broken and reconnected.

Preferably, the flow of the pressurized gas and fluid are controlled by a clamping mechanism that operates from or on the exterior of multi-lumen tubing 155 to controllably clamp, pinch, or otherwise change the cross-sectional flow area of the desired lumen delivering either pressurized gas, fluid, or both. Such a configuration does not require breaking and reconnecting the pressurized gas and liquid channels of multi-lumen tubing 155. In a preferred embodiment, the flow control mechanism includes at least one slide, roller, or pivoting member which is positionable or moveable in relation to an angled surface or ramp to restrict or clamp a section of flexible tubing between the slide or roller and the ramp. The flow control mechanism may have separate slides or rollers for the pressurized gas and fluid channels or may have a single slide or roller which clamps both.

Figure 7:
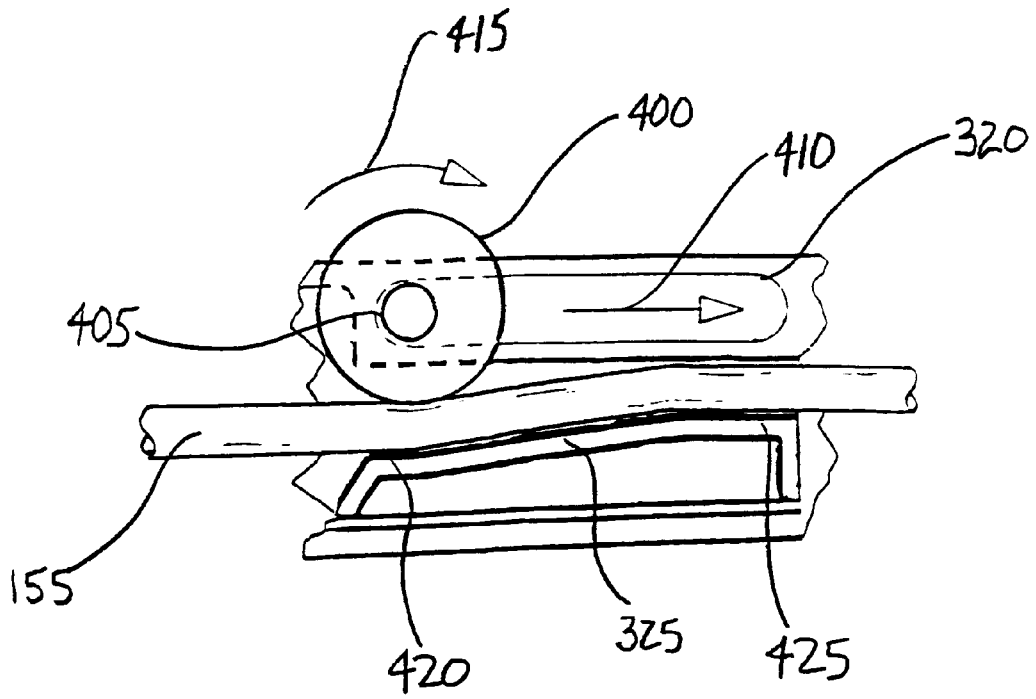
FIGS. 7 and 8 are partial plan views showing a flow control mechanism in an open condition and a substantially closed condition.
Figure 8:
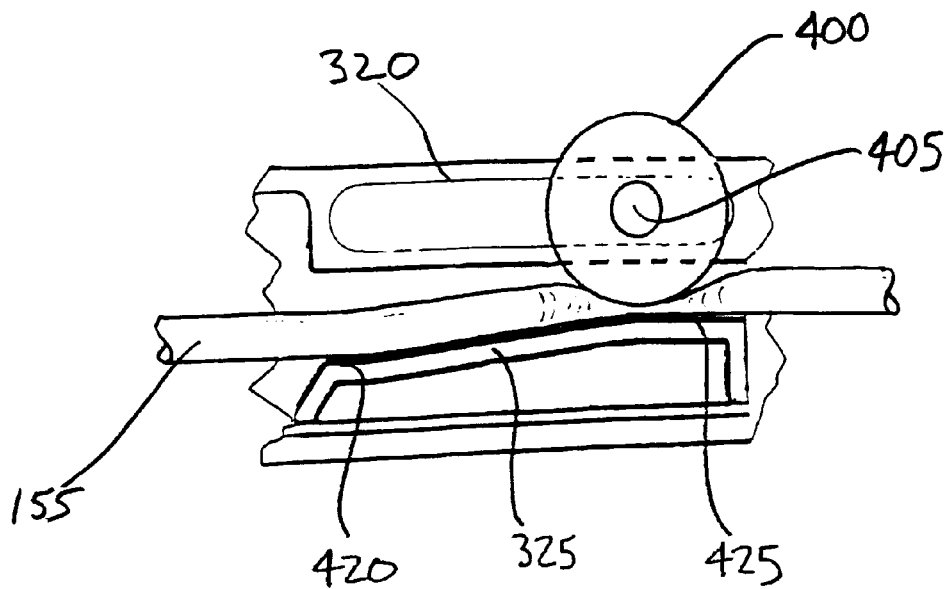

A preferred flow control mechanism is illustrated in FIGS. 7 and 8. The flow control mechanism generally includes ramp 325 for supporting a length of multi-lumen tubing 155 and actuator or roller 400 which is constrained to move relative to ramp 325 in a manner which allows its distance to ramp 325 to be selectively increased or decreased. Multi-lumen tubing 155 is positioned between roller 400 and ramp 325 such that when the distance between the roller 400 and ramp 325 is decreased, multi-lumen tubing 155 is compressed or clamped between ramp 325 and roller 400, thus causing the cross-sectional flow area of one or both of the pressurized gas and fluid channels to be altered.

Preferably, the movement of roller 400 is constrained by one or more slots 320 which is positioned in an angular relationship to at least a portion of ramp 325. Preferably roller 400 has an axle or hubs 405 on each side which are free to translate and rotate within their respective slots. From a beginning or open position as shown in FIG. 7, roller 400 may be rotated by the user in the direction of arrow 415, causing roller 400 to proceed in the direction indicated by arrow 410 and moving closer to ramp 325, thus constricting multi-lumen tubing 155. At some point, the distance between roller 400 and ramp 325 becomes sufficiently small so as to completely interrupt or close off substantially all flow from multi-lumen tubing 155.

The angle 430 of ramp 325 with respect to slot 320 is preferably low enough to ensure that the position of roller 400 is self-locking. That is, roller 400, when released by the user at any position along ramp 325, is held in place by friction from moving backwards and releasing the pressure against multi-lumen tubing 155. Ramp 325 may also include sections oriented at various angles or sections which are curved with respect to slot 325 to alter the rate at which multi-lumen tubing 155 is clamped with respect to the amount of movement of roller 400. In a preferred embodiment, angle 430 of ramp 325 is in the range of about 4° to about 20°, more preferably from about 4° to about 8°. Further, it is preferred that the angle converges distally so that pressure existing in the flexible tubing may urge the roller towards the apex of the angle.

Ramp 325 may further include a first section 420 corresponding to an open position of roller 400 and a second section 425 corresponding to a closed or clamped position of roller 400. In a preferred embodiment first section 420 and second section 425 are oriented substantially parallel to slot 320. Such a configuration provides tactile feedback to the user when the roller is in the fully open and fully closed positions. Second section 425 associated with the closed or fully clamped position of roller 400, further ensures that roller 400 will not become accidentally displaced from the closed position.

When used in conjunction with flexible multi-lumen tubing 155, a single flow control mechanism as just described may be used to control both the pressurized gas and the fluid for presentation of an optimal directed stream at the target site. As multi-lumen tubing 155 is compressed between roller 400 and ramp 325 as the roller is advanced in the direction indicated by arrow 410, both the pressurized gas lumen and the fluid lumen may be configured such that their cross-sectional area collapse or constrict in a relatively proportional manner. In the alternative, the cross-sectional flow area of the pressurized gas lumen and the fluid lumen may be configured to constrict differentially with respect to each other in response to being compressed between roller 400 and ramp 325.

Preferably, the cross-sectional flow area of the pressurized gas lumen of multi-lumen tubing 155 is configured to decrease, at least initially, at a substantially greater rate than that of the fluid lumen, until both the pressurized gas and the fluid lumen become completely closed or constricted as roller 400 reaches the closed position. With the flow control mechanism and multi-lumen tubing constructed in such a manner, the flow rate of the pressurized gas can be adjusted largely independent of the fluid flow rate. This may be particularly desirable for in-use flow adjustments because the pressurized gas is somewhat compressible and is typically supplied at a much greater pressure than the fluid.

Figure 9:
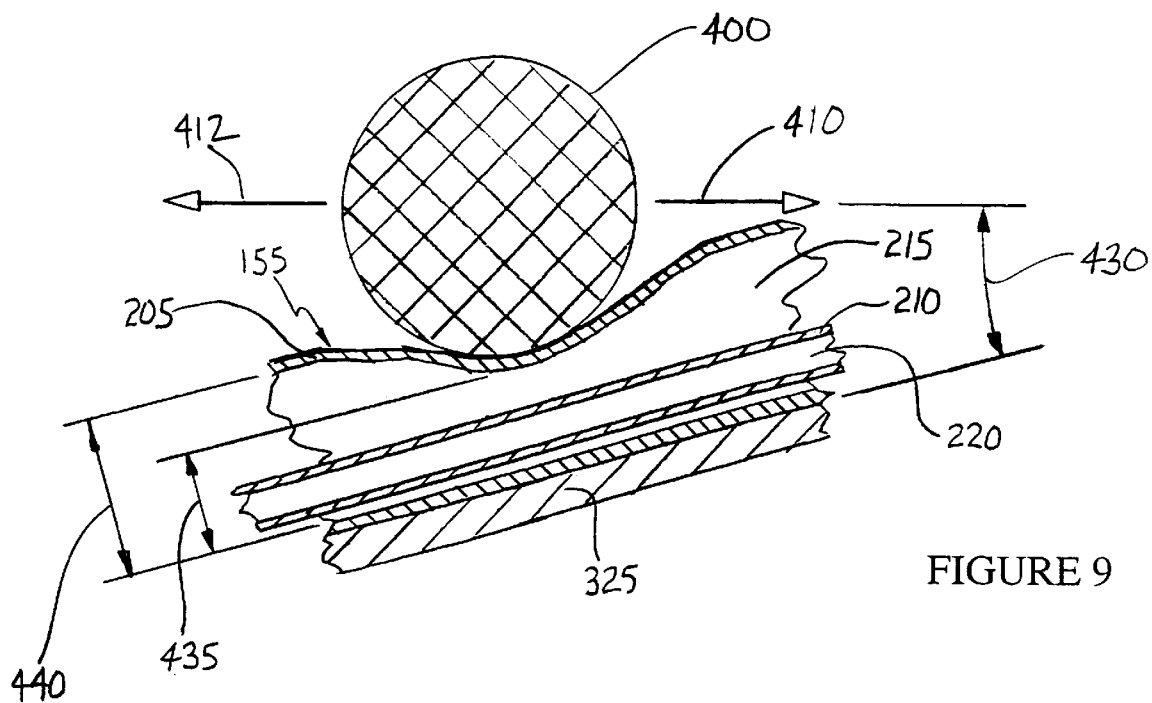
FIG. 9 is a cross-sectional view illustrating a preferred flow control mechanism in accordance with the principles of the present invention.

FIG. 9 illustrates a preferred embodiment, in which roller 400 and ramp 325 is used in conjunction with multi-lumen tubing 155 having a coaxial arrangement, such as that shown and described above. Roller 400 is shown in a position between the open position and the closed position in which multi-lumen tubing 155 is being partially compressed between roller 400 and ramp 325. With the roller in this intermediate position the cross-sectional flow area of outer tube 205 and corresponding gas lumen 215 has been compressed from a first height 440 to a second height 435. At the same time, inner tube 210 and corresponding fluid lumen 220 remains undisturbed. Thus, within a range of intermediate positions, roller 400 may be moved in a direction indicated by arrow 410 to reduce gas flow relative to the undisturbed fluid flow or may be moved in a direction indicated by arrow 412 to increase gas flow relative to the undisturbed fluid flow. As roller 400 is moved near the closed position, the cross-sectional flow area of both gas lumen 215 and fluid lumen 220 are affected, and begin to close until all flow is finally stopped.

Preferably, handpiece assembly 165 has defined or formed therein flow control housing 185 in which roller 400 and ramp 325 are situated. In a preferred embodiment, slot 320 and ramp 325 are integral with or molded in features of first half 180 or second half 182 (or both) of handpiece assembly 165 as shown in the Figures. The distal delivery unit then becomes a simple, cost effective assembly that requires only securing first and second handpiece halves 180 and 182 over the internal tubing elements (multi-lumen tubing 155, connector 350, or distal delivery shaft 160, depending on the configuration) and roller 400.

Typically, some portion of the periphery of roller 400 is accessible through first and second handpiece halves 180 and 182. This allows the user to conveniently actuate the flow control mechanism while holding and manipulating the distal delivery unit at the surgical site. In a preferred embodiment, the peripheral surface of the roller has features to provide an enhanced grip.

Figure 10:
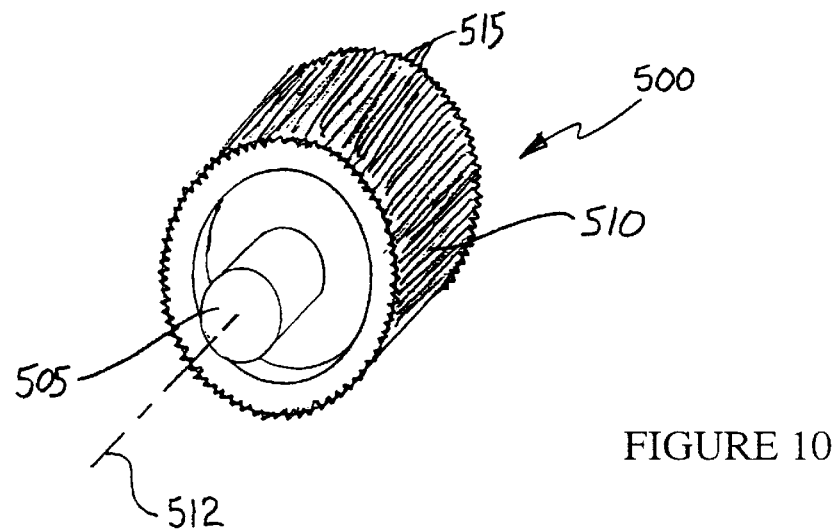
FIG. 10 is a perspective view illustrating a preferred flow control actuator.

A preferred roller having gripping features on its outside periphery is shown in FIG. 10. Roller 500 has a generally cylindrical shape having a central axis 512 and an outer periphery or surface 510. Roller 500 has hub shaft or axle 505 which is generally concentric with central axis 512 and having a first end and a second end (not visible in FIG. 10) for supporting roller 500 between a pair of spaced, parallel slots. Surface 510 may have raised or recessed features constructed to provide a higher friction grip against the exterior of the flexible tubing, the operation by the user, or both. In a preferred embodiment, roller 500 has a number of ridges or teeth 515 around surface 510. Preferably, teeth 515 are substantially parallel to the axis of hubs 505 upon which roller 500 rotates.

The directed stream blower system of the present invention provides greatly improved flow control. In use, the directed stream blower system is connected to the appropriate sources of pressurized gas and sterile fluid. Preferably, the pressurized gas is regulated at a pressure of about 50 pounds/in$^2$ or less. Pinch clamp 120 is opened and an initial sterile liquid flow rate may be established using optional roller clamp 125. The user grasps handpiece assembly 165, typically with one hand, and positions delivery shaft 160 and tip 170 at a desired position adjacent a target surgical site to be cleared. With the same hand that is grasping and manipulating handpiece assembly 165, actuator 190 may be manipulated to adjust the flow of the pressurized gas or the fluid or both, depending on the construction of the flow control, to obtain a desirable directed stream for optimally clearing the surgical site. Actuator 190 may be manipulated to completely interrupt substantially all gas and fluid flow at any time as may be desired. Flow control can be advantageously performed without distraction by the user while the surgical site is being cleared.

While this invention has been described with reference to certain illustrative embodiments, this description is not intended to be construed in a limiting sense. Various modifications to and combinations of the illustrative embodiments, as well as other embodiments of the invention will be apparent to persons skilled in the art upon reference to the description. Accordingly, the invention is not to be restricted except by the claims which follow.

What is claimed is:

1. A surgical blower for providing a directed stream for clearing a surgical site, said blower comprising:
    an elongated flexible tube having a first lumen and a second lumen, said second lumen being separate and independent of said first lumen; and
    a handle having an interior passage for receiving a length of said flexible tube, a surface adapted to support at least a portion of said length, and a roller positionable in relation to said surface;
    said portion of said length being positioned within said passage between said surface and said roller such that movement of said roller closer to said surface at least partially clamps said portion of said length.

2. The surgical blower of claim 1 wherein said first lumen and said second lumen are coaxial.

3. The surgical blower of claim 1 wherein said flexible tube comprises an outer tube having an inside diameter and a central lumen therein and an inner tube having an outside diameter and said second lumen therein, said inner tube being positioned within said central lumen, said first lumen being the space between said inside diameter and said outside diameter.

4. The surgical blower of claim 3 wherein said outer tube is made of a first material and said inner tube is made of a second material.

5. The surgical blower of claim 1 wherein said roller is substantially cylindrical having a central axis and a central hub shaft concentric with said central axis, and wherein said handle further comprises at least one slot oriented at an angle to said surface, said hub shaft being constrained within said at least one slot.

6. The surgical blower of claim 5 wherein said angle is between about 4° to about 8°.

7. The surgical blower of claim 5 wherein said hub shaft has a first end and a second end and said handle has a first slot and a second slot parallel to said first slot, said first end being constrained within said first slot and said second end being constrained within said second slot.

8. The surgical blower of claim 1 wherein said first lumen has a proximal end and a distal end, said second lumen has a proximal end and a distal end, said proximal end of said first lumen being connected to a source of pressurized gas, and said proximal end of said second lumen being connected to a source of fluid, said surgical blower further comprising a malleable tube having a proximal portion positioned within said interior passage and a distal end for placement adjacent said surgical site, said distal end of said first lumen being fluidly coupled to said proximal portion of said malleable tube, said second lumen extending through at least a portion of said malleable tube.

9. The surgical blower of claim 7 wherein said first lumen and said second lumen are co-axial.

10. A surgical blower for providing a directed stream for clearing a surgical site, said blower comprising:
    a handle having a surface adapted to support a length of flexible tubing;
    an articulating actuator associated with said handle, said actuator being moveable relative to said surface from at least a first position at a first distance from said surface to a second position at a second distance relative to said surface; and
    a section of flexible tubing positioned between said surface and said actuator; said flexible tubing having a first lumen in fluid communication with a source of pressurized gas, and a second lumen in fluid communication with a source of sterile fluid, said first lumen being co-axial with said second lumen, said flexible tubing having an outside dimension greater than said second distance.

11. The surgical blower according to claim 10, wherein said articulating actuator is a roller constrained within at least one slot, said at least one slot being at an angle relative to said surface.

12. The surgical blower of claim 11 wherein said roller is substantially cylindrical having an outer surface, said roller having a plurality of teeth formed in said outer surface.

13. A surgical blower for providing a directed stream for clearing a surgical site, said blower comprising:
    a handle having a proximal opening a distal opening and a channel extending therebetween;
    a malleable tube having a proximal end portion secured within said channel and a distal end portion for placement adjacent said surgical site; and
    an elongated flexible tube having a first lumen having a proximal end and a distal end and a second lumen having a proximal end and a distal end, said proximal end of said first lumen being connected to a source of pressurized gas, said proximal end of said second lumen being connected to a source of fluid, said distal end of said first lumen being fluidly coupled to said malleable tube, said second lumen extending through at least a portion of said malleable tube.

14. The surgical blower of claim 13 wherein said first lumen and said second lumen are co-axial.

15. The surgical blower of claim 13 wherein said flexible tube comprises an outer tube having a central lumen and an inner tube positioned within said central lumen.

16. The surgical blower of claim 13 wherein said distal end of second lumen terminates distally of said malleable tube.

17. The surgical blower of claim 13 wherein said handle further comprises a ramp, at least one slot at an angle with respect to said ramp, and a roller having a central hub constrained for movement within said at least one slot from at least a first position at a first distance from said ramp to a second position at a second distance from said ramp, said flexible tube being positioned between said ramp and said roller, said flexible tube having an outside dimension greater than said second distance.

18. The surgical blower of claim 13 wherein said malleable tube is made of stainless steel.

19. The surgical blower of claim 18 further comprising a polymeric layer covering substantially all of said malleable tube.

* * * * *